(12) United States Patent
Kim et al.

(10) Patent No.: US 12,703,669 B2
(45) **Date of Patent: *Aug. 11, 2026**

(54) FABRICATION OF POLYCHROMATIC/POLYTRANSLUCENT ZIRCONIA BLOCK FROM PRE-SHADED ZrO2 BLOCK BY INFILTRATION

(71) Applicant: James R. Glidewell Dental Ceramics, Inc., Newport Beach, CA (US)

(72) Inventors: Dongkyu Kim, Irvine, CA (US); Rajashekharam V. Malyala, Camarillo, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/189,553

(22) Filed: Mar. 24, 2023

(65) Prior Publication Data

US 2023/0303459 A1 Sep. 28, 2023

Related U.S. Application Data

(60) Provisional application No. 63/324,439, filed on Mar. 28, 2022.

(51) Int. Cl.
*A61C 13/08* (2006.01)
*A61C 13/083* (2006.01)
(Continued)

(52) U.S. Cl.
CPC .......... *C04B 41/457* (2013.01); *A61C 13/082* (2013.01); *A61C 13/083* (2013.01); *A61K 6/16* (2020.01); *A61K 6/818* (2020.01); *C04B 35/48* (2013.01); *C04B 41/0072* (2013.01); *C04B 41/4535* (2013.01); *C04B 41/5045* (2013.01); *C04B 41/87* (2013.01);
(Continued)

(58) Field of Classification Search
None
See application file for complete search history.

(56) References Cited

U.S. PATENT DOCUMENTS 7,845,924 B2 12/2010 Cadario et al.
7,981,531 B2 7/2011 Rheinberger et al.
(Continued)

FOREIGN PATENT DOCUMENTS

JP 2017128466 A * 7/2017
WO 2004031103 A1 4/2004
(Continued)

OTHER PUBLICATIONS

Kim et al. "Optical properties of pre-colored dental monolithic zirconia ceramics". Journal of Dentistry 55 (2016) 75-81. (Year: 2016).*

(Continued)

*Primary Examiner* — Jose I Hernandez-Kenney
(74) *Attorney, Agent, or Firm* — Klarquist Sparkman, LLP

(57) ABSTRACT

A pre-shaded $ZrO_2$ block (e.g., a monochromatic block or polychromatic block) is sequentially infiltrated with a yttrium-containing solution at one porous surface and with water at a second porous surface to make a polychromatic/polytranslucent $ZrO_2$ block.

10 Claims, 10 Drawing Sheets

(51) Int. Cl.

| | |
|---|---|
| ***A61K 6/16*** | (2020.01) |
| ***A61K 6/818*** | (2020.01) |
| ***C04B 35/48*** | (2006.01) |
| ***C04B 41/00*** | (2006.01) |
| ***C04B 41/45*** | (2006.01) |
| ***C04B 41/50*** | (2006.01) |
| ***C04B 41/87*** | (2006.01) |

(52) U.S. Cl.

CPC ................. *C04B 2235/3225* (2013.01); *C04B 2235/3246* (2013.01); *C04B 2235/616* (2013.01); *C04B 2235/9661* (2013.01)

(56) References Cited

U.S. PATENT DOCUMENTS

| | | | | |
|---|---|---|---|---|
| 8,025,992 | B2 | 9/2011 | Engels et al. | |
| 8,298,329 | B2 | 10/2012 | Knapp et al. | |
| 8,721,336 | B2 | 5/2014 | Rheinberger et al. | |
| 8,936,848 | B2 | 1/2015 | Jung et al. | |
| 8,962,146 | B2 | 2/2015 | Giordano | |
| 9,039,947 | B2 | 5/2015 | Jahns et al. | |
| 9,095,403 | B2 | 8/2015 | Carden et al. | |
| 9,212,065 | B2 | 12/2015 | Yamada et al. | |
| 9,365,459 | B2 | 6/2016 | Carden et al. | |
| 9,434,651 | B2 | 9/2016 | Carden | |
| D769,449 | S | 10/2016 | Leeson et al. | |
| 9,512,317 | B2 | 12/2016 | Carden et al. | |
| 9,649,179 | B2 | 5/2017 | Jung et al. | |
| 9,872,746 | B2 * | 1/2018 | Hauptmann ............ | A61C 5/77 |
| 9,949,808 | B2 | 4/2018 | Wolz | |
| 10,034,728 | B2 | 7/2018 | Jung et al. | |
| 2005/0175552 | A1 | 8/2005 | Hoic et al. | |
| 2008/0241551 | A1 | 10/2008 | Zhang et al. | |
| 2013/0316305 | A1 | 11/2013 | Carden et al. | |
| 2015/0173869 | A1 | 6/2015 | Jung et al. | |
| 2015/0223917 | A1 | 8/2015 | Herrmann et al. | |
| 2016/0120765 | A1 | 5/2016 | Dang et al. | |
| 2016/0228223 | A1 | 8/2016 | Jung | |
| 2017/0157645 | A1 | 6/2017 | Wolz | |
| 2017/0189143 | A1 | 7/2017 | Wolz | |
| 2017/0245970 | A1 | 8/2017 | Jung et al. | |
| 2017/0304031 | A1 | 10/2017 | Jung et al. | |
| 2017/0304032 | A1 | 10/2017 | Jung et al. | |
| 2019/0233340 | A1 * | 8/2019 | Kim .................... | C04B 41/5007 |
| 2021/0230077 | A1 | 7/2021 | Kim et al. | |

FOREIGN PATENT DOCUMENTS

| | | | |
|---|---|---|---|
| WO | 2004103303 | A1 | 12/2004 |
| WO | 2014206439 | A1 | 12/2014 |

OTHER PUBLICATIONS

By "Chroma." Merriam-Webster.com Dictionary, Merriam-Webster, https://www.merriam-webster.com/dictionary/chroma. Jul. 4, 2022. (Year: 2022).*

McKinley, Jenna. "A Guide to Color". New Mexico State University, https://pubs.nmsu.edu/. Mar. 2018 (Year: 2018).*

McIntyre, Carol. "What Are the Three Characteristics of Every Color?". https://www.celebratingcolor.com/. May 25, 2018 (Year: 2018).*

Guanwei Liu et al., Fabrication of coloured zirconia ceramics by infiltrating water debound injection moulded green body, Research Gate, Advances in Applied Ceramics, Jan. 2011, in 6 pages.

* cited by examiner

FABRICATION OF POLYCHROMATIC/POLYTRANSLUCENT ZIRCONIA BLOCK FROM PRE-SHADED ZrO2 BLOCK BY INFILTRATION

This application claims the benefit of and priority to U.S. Provisional Patent Application No. 63/324,439, filed Mar. 28, 2022, which is incorporated herein by reference in its entirety.

BACKGROUND

Dental restorations are currently milled from a monochromatically colored block and then hand-painted to match a patient's natural tooth color to achieve a natural aesthetic appearance. However, this process is labor-intensive, time-consuming, and costly. The process also depends largely on the skill of the dental technician leading to inconsistent results.

SUMMARY

Disclosed herein is a method comprising:

(a) obtaining a pre-shaded porous ceramic body comprising
   i. a first end surface adjacent a first porous region, and
   ii. a second end surface adjacent a second porous region, opposite the first end surface; and (b)(1) infiltrating a yttrium-containing solution through the first end surface to occupy the first porous region adjacent the first end;

(c)(1) inverting the yttrium-containing solution-infiltrated ceramic body;

(d)(1) infiltrating water through the second end surface to occupy the second porous region adjacent the second end;

(e)(1) contacting a portion of the yttrium-containing solution in the first porous region with a portion of the infiltrating water in the second porous region at an interface; and (f)(1) forming within the interface a color/translucency gradient region resulting in a polychromatic/polytranslucent block; or (b)(2) infiltrating (i) water or (ii) a water-containing mixture that has a higher viscosity than the viscosity of water alone through the first end surface to occupy the first porous region adjacent the first end;

(c)(2) infiltrating a yttrium-containing solution through the first end surface of the first porous region adjacent the first end to occupy the first porous region adjacent the first end;

(d)(2) inverting the water or water-containing mixture and the yttrium-containing solution-infiltrated ceramic body;

(e)(2) contacting a portion of the yttrium-containing solution in the first porous region with a portion of the infiltrating water or water-containing mixture in the first porous region at an interface; and (f)(2) forming within the interface a color/translucency gradient region resulting in a polychromatic/polytranslucent block.

Also disclosed herein is a method comprising:

(a) positioning a porous ceramic body within a casing, wherein the casing has a side wall and a bottom, and wherein the porous ceramic body comprises a side surface, a first end surface adjacent a first porous region, and a second end surface adjacent a second porous region opposite the first end surface, and the bottom and the side wall of the casing contact the second end surface and side surface of the porous ceramic body such that the side wall of the casing extends beyond the first end surface of the porous ceramic body and forms a reservoir;

(b) providing a volume of a yttrium-containing solution within the reservoir on the first end surface of the porous ceramic body;

(c) infiltrating the yttrium-containing solution through the first end surface of the ceramic body into a first porous region of the porous ceramic body, wherein the casing material prevents the yttrium-containing solution from passing through the second end surface and the side surface of the porous ceramic body;

(d) inverting the porous ceramic body within the casing, wherein the first end surface is in contact with the bottom of the casing, and the side wall of the casing conforms to and contacts the side surface of the porous ceramic body;

(e) providing a volume of water within the reservoir on the second end surface;

(f) infiltrating the water through the second end surface into a second porous region that is adjacent the first porous region, wherein the casing material prevents the yttrium-containing solution and the water from passing through the first end surface and the side surface of the porous ceramic body;

(g) contacting a portion of the water in the second porous region with a portion of the yttrium-containing solution in the first porous region, and then mixing to form a color/translucency gradient region and (h) sintering the infiltrated porous ceramic body to form a sintered ceramic body comprising a first color/translucency region adjacent the first end surface, a second color/translucency region adjacent the second end surface, and a color/translucency gradient region there between.

Further disclosed herein is a method comprising:

(a) positioning a porous ceramic body within a casing, wherein the casing has a side wall and a bottom, and wherein the porous ceramic body comprises a side surface, a first end surface adjacent a first porous region, and a second end surface adjacent a second porous region opposite the first end surface, and the bottom and the side wall of the casing contact the second end surface and side surface of the porous ceramic body such that the side wall of the casing extends beyond the first end surface of the porous ceramic body and forms a reservoir;

(b) providing a volume of water or a water-containing mixture within the reservoir on the first end surface of the porous ceramic body;

(c) infiltrating the water or water-containing mixture through the first end surface of the ceramic body into a first porous region of the porous ceramic body, wherein the casing material prevents the water or water-containing mixture from passing through the second end surface and the side surface of the porous ceramic body;

(d) infiltrating a yttrium-containing solution through the first end surface of the ceramic body into the first porous region of the porous ceramic body, wherein the casing material prevents the yttrium-containing solution and the water or water-containing mixture from passing through the second end surface and the side surface of the porous ceramic body;

(e) inverting the infiltrated ceramic body within the casing thereby mixing the infiltrated water or water-containing mixture with the infiltrated yttrium-containing solution; and (f) sintering the infiltrated porous ceramic body to form a sintered ceramic body comprising a first color/translucency region adjacent the first end surface, a second color/translucency region adjacent the second end surface, and a color/translucency gradient region there between.

The foregoing will become more apparent from the following detailed description, which proceeds with reference to the accompanying figures.

BRIEF DESCRIPTION OF THE DRAWINGS

FIG. 5 (B) Optical micrograph of the three anterior crowns. left: milled from pre-shaded block, middle: milled from block infiltrated only with yttrium nitrate solution at one porous surface, right: milled from a block sequentially infiltrated with yttrium nitrate solution and water.

DETAILED DESCRIPTION

Figure 1:
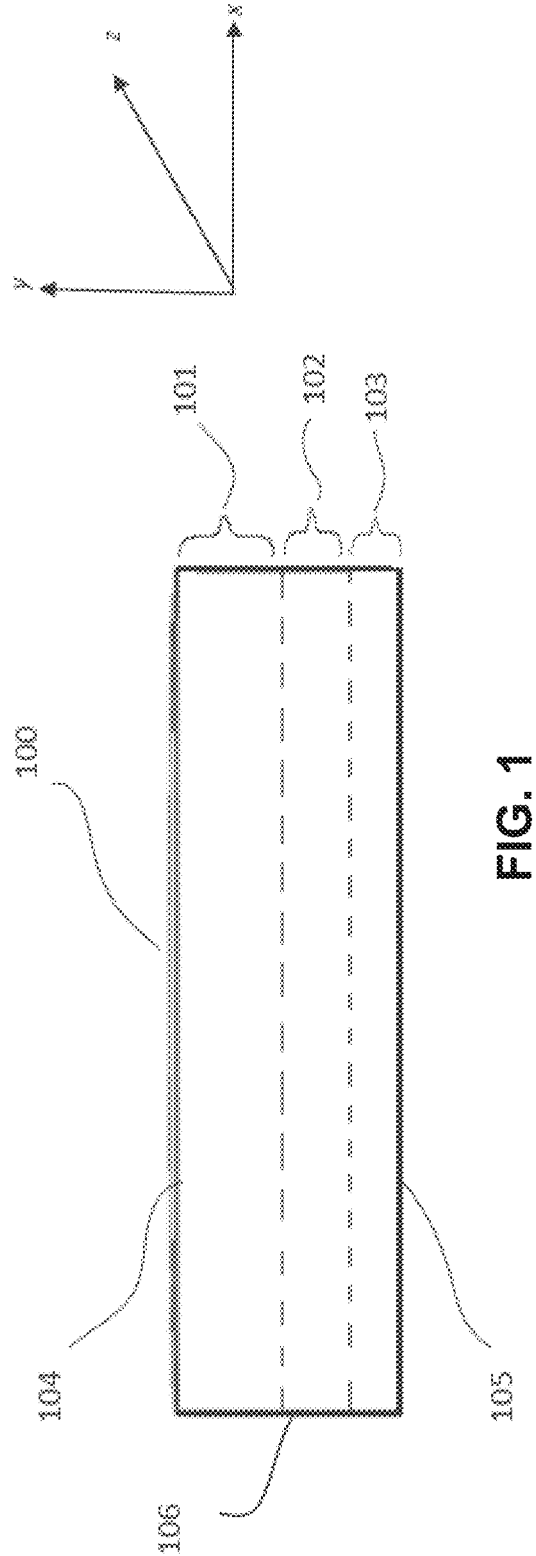
FIG. 1 is a perspective view of an embodiment of a sectioned polychromatic/polytranslucent body.

A pre-shaded $ZrO_2$ block (i.e., a monochromatic or polychromatic block) is sequentially infiltrated with a yttrium-containing solution (e.g., a yttrium nitrate solution or yttrium chloride solution) at a porous surface and with water at a porous surface to make a polychromatic/polytranslucent $ZrO_2$ block. The resulting polychromatic/polytranslucent $ZrO_2$ block has higher translucency and weakened color in the incisal region, lower translucency and stronger color in the cervical area, and a smooth translucency and color gradient at an interfacial transition region. Polychromatic/polytranslucent $ZrO_2$ dental restorations can be milled from the sequentially infiltrated blocks.

The yttrium-containing solution is a solution of at least one yttrium compound. Illustrative yttrium compounds include yttrium nitrate, yttrium chloride, yttrium carbonate, yttrium acetate, or any other soluble yttrium-containing material. The solvent(s) in the yttrium-containing solution can be a polar or non-polar, organic or inorganic solvent, such as water, isopropyl alcohol (IPA), or ethylene glycol.

In certain aspects, a water-containing mixture (e.g., a solution) that has a higher viscosity compared to the viscosity of water alone is utilized in the infiltration process. The mixture includes at least one ingredient that increases the viscosity of the mixture at 25° C. higher than the viscosity of water alone at 25° C. Illustrative ingredients include any liquid that is completely miscible with water and has a higher viscosity than water. Examples of such liquids include organic solvents such as ethylene glycol, polyethylene glycol, glycol, and glycerine. In certain embodiments, the ingredient is present in the mixture in an amount of 10 wt % to 90 wt %, or 20 wt % to 70 wt %, or 30 wt % to 50 wt %, based on the total weight of the mixture. The higher viscosity water-containing mixture provides more control over the diffusion speed resulting in a more spatially narrowed interfacial transition region.

In one aspect, a pre-shaded $ZrO_2$ block (i.e., a monochromatic or polychromatic block) is sequentially infiltrated with a yttrium nitrate solution at one porous surface and with water at a second porous surface to make a polychromatic/polytranslucent $ZrO_2$ block.

For example, pre-shaded $ZrO_2$ block is placed in an infiltration setup and yttrium-containing solution is infiltrated into the block by placing the yttrium-containing solution on the top of the block for a predetermined period of time. In certain embodiments, the yttrium-containing solution infiltration time is 10 seconds to 120 minutes, more particularly 1 minute to 60 minutes, and most particularly 3 minutes to 30 minutes. The excess yttrium-containing solution that remains on the top of the block, if any, is removed, and then the block is inverted inside of the setup. Water is poured onto the $ZrO_2$ block on a surface that is faced opposite to the surface that was initially subjected to the yttrium-containing solution, and the water is infiltrated into the block for a predetermined period of time. In certain embodiments, the water infiltration time is 30 seconds to 180 minutes, more particularly 1 minute to 120 minutes, and most particularly 3 minutes to 60 minutes. In certain embodiments, the water infiltration time is longer than the yttrium-containing solution infiltration time. Excess water, if any, is removed and then the surface of the block is cleaned. The infiltrated water diffuses down and contacts the previously infiltrated yttrium-containing solution, resulting in formation of the smooth color and translucency gradient in the transition region. The transition region forms a smooth color/translucency gradient lacking discernable color/translucency transition lines between the transition region and the upper and lower regions, when viewed with the unaided eye. The infiltrated yttrium-containing solution in the incisal region increases translucency, and also weakens color in the incisal region resulting in formation of polychromatic/polytranslucent blocks.

In another example, water or higher viscosity water-containing mixture is infiltrated into the ceramic body prior to infiltrating with the yttrium-containing solution. In one aspect, pre-shaded $ZrO_2$ block is placed in an infiltration setup and water or higher viscosity water-containing mixture is infiltrated into the block by placing the water or higher viscosity water-containing mixture on the top of the block for a predetermined time period. In certain embodiments, the water or higher viscosity water-containing mixture infiltration time is 3 seconds to 30 minutes, more particularly 5 seconds to 15 minutes, and most particularly 10 seconds to 5 minutes. The excess water or higher viscosity water-containing mixture that remains on the top of the block, if any, is removed. The yttrium-containing solution then is poured onto the $ZrO_2$ block. The yttrium-containing solution is poured onto the same surface that was initially subjected to the water or higher viscosity water-containing mixture. In certain embodiments, the yttrium-containing solution infiltration time is 10 seconds to 120 minutes, more particularly 1 minute to 60 minutes, and most particularly 3 minutes to 60 minutes. In certain embodiments, the water or water-containing mixture infiltration time is shorter than the yttrium-containing infiltration time. After the yttrium-containing solution infiltration, the block is inverted and the water or higher viscosity water-containing mixture diffuses into the yttrium-containing solution.

In certain embodiments, the polychromatic/polytranslucent ceramic bodies comprises two or more color/translucency regions arranged from the top surface of the ceramic body to bottom surface (y-axis direction). A transition region comprising a smooth color gradient and a smooth translucency gradient is located between the two color/translucency regions. Each color/translucency region may comprise substantially uniform color and translucency across the diameter or width of a ceramic body. The ceramic body may be any shape, including but not limited to, cylinder, disc, or polyhedron, such as a cube or prism, or an irregular shape. In some embodiments, the ceramic body may be in the shape of a dental restoration preform such as those described in U.S. Design Pat. Nos. 769,449, 781,428, 939,712, and U.S. Design patent application Ser. No. 29/790,332, filed on Nov. 19, 2021.

Color regions of a millable ceramic block may be tailored to provide a first color or shade at a top region of the ceramic block and a second color or shade that is lighter than the first color or shade at a bottom region. A computer design of a dental restoration, such as a restoration tooth or denture design, may be nested so that a cervical and/or body region is milled from a darker shaded top portion, and an incisal region is milled from the lighter shaded bottom portion. The lighter, bottom region has greater translucency than the top region, creating a natural incisal appearance in a finished dental restoration. Advantageously, a color transition region eliminates sharp boundaries between two color regions that may occur in traditional processes. The resulting dental restorations may comprise a smooth color or shade gradient between the body region and incisal region of a restoration tooth.

In an exemplary embodiment, illustrated in FIG. 1, a polychromatic/polytranslucent ceramic body (100) comprises two or more color/translucency regions (101,103) and a color/translucency transition region (102) providing a smooth color/translucency gradient there between. In this embodiment, individual color/translucency regions (101, 103) and color/translucency transition region (102) (illustrated in FIG. 1 by broken lines) are arranged from a top surface (104) of the ceramic body to a bottom surface (105) along an axis (referred to herein as y-axis direction, as illustrated in FIG. 1). A color/translucency transition region (102) provides a gradual transition between the color/translucency of a first region (101) and the color/translucency of a second region (103). As illustrated in FIG. 1, three color/translucency regions (101, 102, 103) extend between outer side surfaces (106) across the width or diameter (x and z axis direction) of the ceramic body, for a selected height (in the y-axis direction).

The polychromatic ceramic body, illustrated in FIG. 1 as a disc-shaped body, may be any shape suitable for use in making dental restorations. In one embodiment, a dental restoration crown milled from the polychromatic/polytranslucent ceramic body, comprises a cervical or a body region (e.g., adjacent the gingiva when installed) that is milled from a darker color/lower translucency region (101), and an incisal region (e.g. adjacent an incisal edge) that is milled from a lighter color/higher translucency region (103), of the ceramic body. The crown comprises a smooth color/translucency gradient between cervical/body region and incisal region, providing a natural appearance.

An example of a method for making the polychromatic/polytranslucent ceramic body involves unidirectionally infiltrating a yttrium-containing solution into a portion of the porous ceramic body (in the y-axis direction). Prior to infiltration, the outer side surface (106) and bottom surface (105) are covered with a casing material and the casing material is extends out of the top edge adjacent the top surface (104). Casing material may prevent the flow of the yttrium-containing solution in the x-axis and z-axis directions by inhibiting ingress and/or egress through the side surface(s), and the casing material may also prevent the flow of the yttrium-containing solution in the negative y direction by inhibiting ingress and/or egress through bottom surface, of the porous ceramic body during the infiltration step.

Figure 2A:
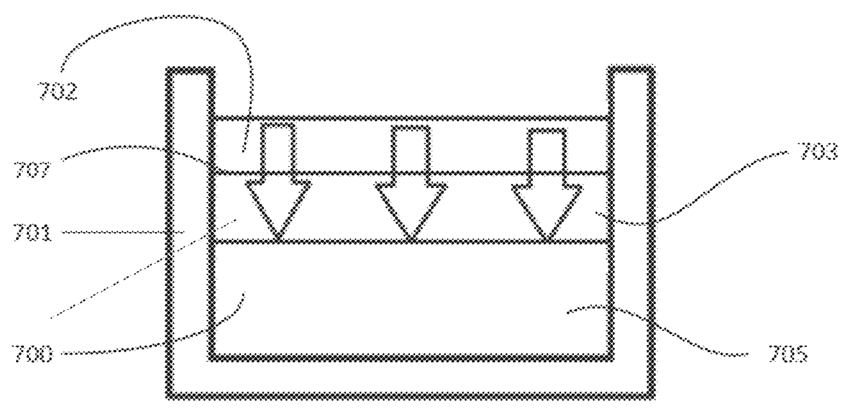
FIGS. 2A, 2B, and 2C, are cross-sectional illustrations of an embodiment of a sequential, unidirectional infiltration process for making a polychromatic/polytranslucent ceramic body having a transition region between two different color/translucency regions.

The yttrium-containing solution is held in a reservoir in contact with the top surface of the porous, ceramic body during the infiltration process. The reservoir is formed by the casing that extends out of the top edge adjacent the top surface of the porous ceramic body as shown in FIG. 2A. The yttrium-containing solution infiltrates into an upper region of the porous ceramic body adjacent the top surface over a period of time. In one embodiment, the infiltration depth of the yttrium-containing solution is at least 1 mm from the top surface, or at least 5 mm from the top surface, or at least 10 mm from the top surface, or between 1 mm and 20 mm from the top surface, or between 5 mm and 14 mm from the top surface, of the ceramic body. In another embodiment, the infiltration depth of the yttrium-containing solution is in the range of 5% to 95%, or 30% to 70%, of the height of the porous ceramic body measured in the y-axis direction from an end surface (e.g. the top surface). Infiltration may proceed for a sufficient time for the yttrium-containing solution to uniformly infiltrate to a desired distance from the infiltration surface. Excess yttrium-containing solution that has not been infiltrated may be removed from contact with the top surface.

The dimensions of the color/translucency regions and color/translucency gradient regions may be designed to be the same or different. In one embodiment, a first color/translucency region, a color/translucency gradient region, and a second color/translucency region each comprise approximately one third of the height (y-axis direction) of a sintered ceramic body, uniformly through the entire width. The dimension of the upper region may be controlled, for example, not only by controlling the volume of water that infiltrates the upper region but also by the degree of diffusion of water into yttrium-containing solution at the interface. The location of the transition region is determined by controlling the relative amount of infiltrated water and yttrium-containing solution. The dimension of the transition region is determined by the degree of diffusion of water down into yttrium-containing solution at the interface. The location of the incisal region is determined by controlling the relative amount of infiltration of water and yttrium-containing solution. The dimension of the incisal region is determined not only by the amounts of infiltrated water and yttrium-containing solution but also by the degree of diffusion of water at the interface between the water and yttrium-containing solution. In certain embodiments, the widths of the cervical region, interface region, and incisal region can be different and can be controlled by altering the relative viscosity of the solvent in yttrium-containing solution to the viscosity of water or the water-containing mixture, thereby providing a different degree of diffusion at the interface. The thickness of the top region, the location and thickness of the transition region, and the location and thickness of the incisal region may slightly change with water diffusion down into yttrium-containing solution until a heating step that removes water or the water-containing mixture and prevents further diffusion of water or higher viscosity water-containing mixture down into the yttrium-containing solution.

Figure 2B:
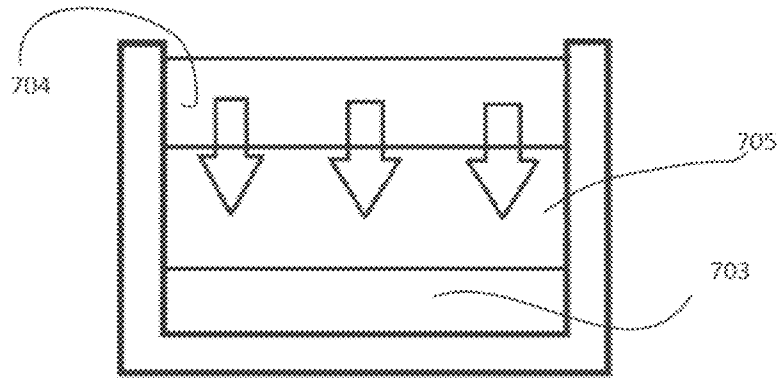
Figure 2C:
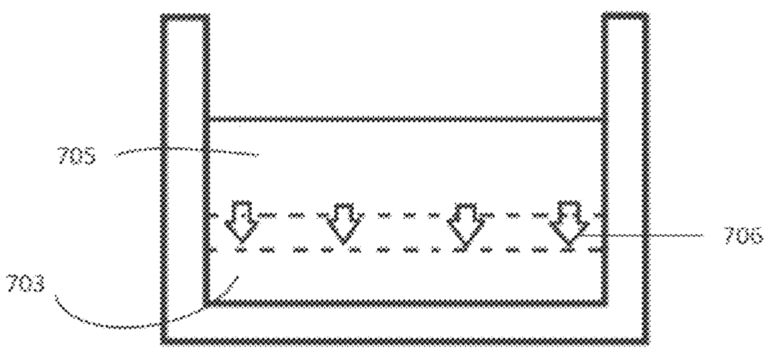

In a further embodiment, illustrated in FIGS. 2A, 2B, and 2C, a sequential, unidirectional infiltration process is provided. In this embodiment, a porous ceramic body (700) is placed within a permeation-resistant casing material (701), wherein a first porous region (703) is positioned above a second porous region (705). In a first step, a volume of yttrium-containing solution (702) in contact with an upward-facing (top) surface (707) of a porous ceramic body (700), is unidirectionally infiltrated (as indicated by the arrows) in a downward direction into the first porous region (703) of the ceramic body (700). After infiltration, the ceramic body is inverted, so that the first porous region (703) is below the second porous region (705).

In a second infiltration step, as illustrated in FIG. 2B, a volume of water (704) in contact with the porous ceramic body is unidirectionally infiltrated into the second porous region (705). The water (704) infiltrates downward towards the yttrium-containing solution (702) in the first porous region (703), in the direction of the bottom of the ceramic body. Thus, a sequential, unidirectional infiltration process is provided where in a first step, a yttrium-containing solution is infiltrated into the porous ceramic body in a top-to-bottom direction axis), and upon inverting the porous ceramic body, in a second step, water is infiltrated into the porous ceramic body in a top-to-bottom (y-axis) direction.

As illustrated in FIG. 2C, after infiltration of water (704) into the second porous region (705), downward diffusion of the water into the yttrium-containing solution forms a smooth transition region (706).

In this embodiment, where the side and bottom surface of the ceramic body is covered with a permeation resistant casing (701), ingress or egress of the water (704) and the yttrium-containing solution (702) through the side and bottom surface of the ceramic body is prevented. Lateral flow (in x-axis and z-axis directions) of the water and the yttrium-containing solution within the pore volume of the ceramic body is inhibited by unidirectionally infiltration. Upward flow (in negative y-axis direction) of the water and the yttrium-containing solution within the pore volume of the ceramic body is also inhibited by unidirectionally infiltration. While not wishing to be bound by theory, it is believed that in some embodiments, rapid convective mixing of water and the yttrium-containing solution is inhibited as the flow of the liquid components into and out of the side surfaces and bottom surface of the ceramic body is restricted by a casing material. Where casing material covers the bottom and side surfaces, inhibiting ingress or egress of the water and the yttrium-containing solution into or out of the ceramic body, mixing of the water and the yttrium-containing solution may occur slowly through downward diffusion within the porous ceramic body.

The casing method and materials are described in more detail in U.S. Pat. No. 10,974,997, which is incorporated herein by reference. The casing can be a unitary piece which covers both side surfaces and bottom surface. Alternatively, the casing can be two separate pieces, one piece for covering the side surfaces and the other piece for covering the bottom surface.

In one embodiment, the yttrium-containing solution is infiltrated within the porous ceramic body, in an amount between 1 vol % and 75 vol % of the pore volume of the porous ceramic body. In another embodiment, the yttrium-containing solution infiltrates between 3 vol % and 60 vol %, or between 5 vol % and 45 vol %, or between 10 vol % and 30 vol %, of the pore volume of the porous ceramic body.

In certain embodiments, the infiltration process may be performed once per block. In other embodiments, the infiltration process may be performed more than once per block.

In one embodiment, a bisque or partially sintered porous ceramic body that is infiltrated with the yttrium-containing solution and water is heated to a temperature below the sintering temperature of the ceramic for a period of time, to facilitate milling of the infiltrated ceramic body.

The heights (relative to the y-axis) of the one or more color/translucency regions, and the color/translucency gradient region, may be controlled by controlling the relative volumes of yttrium-containing solution and water within the ceramic body. The time allotted for infiltration and mixing is selected to control the depth of downward infiltration and mixing of water into the yttrium-containing solution and the smoothness of the gradient of the transition region in the final sintered ceramic body. The heights (relative to the y-axis) of the one or more color/translucency regions, and the color/translucency gradient region may also be controlled by using different solvents as described above.

Infiltration and mixing may occur at ambient temperature and ambient pressure over a period of time, without modifying or adjusting ambient environmental conditions, such as temperature, pressure or humidity. After infiltration in the first and second regions, the ceramic body may be heated to terminate infiltration and mixing by drying.

After infiltration, the total amount of yttrium ions in the sintered body may be 0.01 wt % to 3 wt %, more particularly be 0.025 wt % to 1.7 wt %, and most particularly be 0.03 wt % to 1.5 wt %, based on the total weight of the sintered body. No water (or other ingredients in admixture with water) remains after sintering.

Porous ceramic bodies include partially consolidated, or pre-sintered, bisque stage bodies, having densities below full theoretical density of the ceramic sintered form. Ceramic materials include, but are not limited to, alumina, zirconia, mullite, magnesia, silica and mixtures thereof. Zirconia ceramic bodies may comprise between 85 wt % and 100 wt % of a zirconia material, or between 90 wt % and 99.7 wt % zirconia material, and, optionally, minor amounts of other materials, such as alumina. Zirconia ceramic material may comprise approximately 85 wt % and approximately 98 wt % zirconia, or stabilized zirconia, based on the total weight of the zirconia ceramic material, or approximately 85 wt % or greater, or approximately 90 wt % or greater, or approximately 95 wt % or greater, zirconia, or stabilized zirconia, based on the total weight of the zirconia ceramic material.

Stabilized zirconia ceramic material includes both fully and partially stabilized zirconia. Stabilized zirconia ceramic powder material suitable for use herein includes, but is not limited to, yttria-stabilized zirconia commercially available from Tosoh USA. Further, zirconia may be stabilized with approximately 0.1 mol % to approximately 8 mol % yttria, or approximately 2 mol % to approximately 6 mol % yttria, or approximately 2 mol % to approximately 6.5 mol % yttria, or approximately 2 mol % to approximately 5.5 mol % yttria, or approximately 2 mol % to approximately 5 mol % yttria, or approximately 2 mol % to approximately 4 mol % yttria.

Ceramic powder may have substantially uniform particle size distribution, for example, an average particle size in a range from approximately 0.005 micron (μm) to approximately 1 μm, or from approximately 0.05 μm to approximately 1 μm. Examples of ceramic material suitable for use herein also include zirconia described in commonly owned U.S. Pat. No. 8,298,329, which is hereby incorporated by reference in its entirety.

Pre-shaded ceramic bodies may be infiltrated with the methods described herein. Pre-shaded ceramic materials include commercially available millable, ceramic blocks that match a specific target shade or a shade range, for example, BruxZir® ceramic blocks (e.g., BruxZir® Shaded 16 series in target shades matching VITA® Classic shades; Glidewell Laboratories, Irvine, CA).

Porous ceramic bodies suitable for use herein include blocks having a shape that includes, but is not limited to, a cube, cylinder, disc, near-net shape, or a porous body in the shape of a final dental restoration. Porous ceramic bodies may be made, for example, by pressing or slip casting ceramic powders, or by automated additive (e.g., 3-D printing) and subtractive (e.g., milling) processes, including CAD and/or CAM processes. Processes include, but are not limited to, those described in commonly owned U.S. Pat. Nos. 9,365,459, 9,434,651, and 9,512,317, all of which are hereby incorporated in their entirety, herein.

Prior to infiltration, the porous ceramic bodies may be partially densified, for example, by heating or pre-sintering to increase the density to below full theoretical density of the material. Pre-sintering methods may be conducted in accordance with manufacturer instructions. In some embodiments, prior to infiltration pre-sintering proceeds by heating at an oven temperature within the range of 700° C. to 1200° C. for 1 to 2 hours. Porous ceramic bodies include those having a density of 30% to 90%, or 50% to 85%, or 40% to 75%, of full theoretical density of the sintered ceramic body, while maintaining sufficient porosity for partial or complete infiltration of the yttrium-containing solution into the porous ceramic body. In some embodiments, the porous ceramic body may comprise at least 20 vol % porosity, or at least 25 vol % porosity. Alternatively, a porous ceramic body may comprise at least 40 vol %, or at least 60 vol %, or between 20 vol % and 80 vol %, porosity, when measured by Archimedes method.

The porous (e.g., bisque stage) ceramic body may be infiltrated with the yttrium-containing solution and the water or higher viscosity water-containing mixture before or after shaping into a dental restoration form. The ceramic bodies may be shaped, for example, as a single unit crown, bridge, partial or full denture, based on the individual requirements of a patient.

A method has been found for improving machinability of an infiltrated ceramic body during a shaping process. In some embodiments, after the infiltration process is complete, and, after the optional drying step to terminate the diffusion, the region infiltrated with yttrium-containing solution has an increased surface hardness that may result in difficulty of milling or grinding, or result in damage to the milling tool. In one embodiment, the method further comprises a post-infiltration heat treatment step. The yttrium-containing solution and water infiltrated porous ceramic body is further heated to a temperature (such as, below a bisquing temperature) that is below the sintering temperature of the ceramic material. In some embodiments, the infiltrated ceramic body may be heated to a temperature between 300° C. and 900° C., or between 500° C. and 800° C., for a period of time between about 30 minutes and 15 hours. In certain embodiments, a yttrium chloride solution eliminates the need for a higher temperature (e.g., greater than 300° C.) after infiltration. For example, a post-infiltration temperature of less than 300° C. may be used with a yttrium chloride solution.

The infiltrated ceramic bodies, optionally heated in a post-infiltration heat treatment step, may be milled into the shape of a dental restoration reducing damage to the milling tool. The bisqued, milled ceramic bodies are heated in a final sintering step to eliminate residual porosity. Ceramic bodies prepared by the methods disclosed herein may be sintered in accordance with instructions of the manufacturer of commercially available ceramic bodies, or by heating at a temperature, for example, between about 1300° C. and 1600° C., for about 2 hours to 48 hours.

In another embodiment, ceramic material infiltrated with yttrium-containing solution and water may be sintered prior to milling into a dental restoration, to provide polychromatic/polytranslucent, millable sintered ceramic bodies. Ceramic materials that are infiltrated and sintered prior to milling may have a net shape or size that fits most dental restorations while eliminating excess material for removal. Examples of suitable shaped forms which may be sintered to full theoretical density prior to shaping may be found in commonly owned U.S. Patent Publication No. 2013/0316305, and U.S. Pat. No. D769,449, both of which are hereby incorporated herein in their entirety.

Sintered ceramic bodies made in accordance with unidirectional infiltration methods have a natural polychromatic/polytranslucent appearance while maintaining sufficient strength suitable for use in anterior and posterior dental applications, as well as full- and partial-arch dentures and bridges. For example, the sintered polychromatic/polytranslucent $ZrO_2$ block may have a strength of 500 MPa to 1500 MPa, more particularly 750 MPa to 1200 MPa in the body region of the block. And the polychromatic/polytranslucent $ZrO_2$ block may have a toughness of 2 to 15, more particularly 3 to 8 $MPa \cdot m^{1/2}$ in the body region of the block. For example, the sintered polychromatic/polytranslucent $ZrO_2$ block may have a strength of 200 MPa to 800 MPa, more particularly 500 MPa to 700 MPa, in the incisal region of the block. And the polychromatic/polytranslucent $ZrO_2$ block may have a toughness of 1 to 7 $MPa \cdot m^{1/2}$, more particularly 2 to 5 $MPa \cdot m^{1/2}$ in the incisal region of the block.

One or more color regions of the final sintered ceramic bodies may, optionally, correspond to a bleached shade, or a classical shade, for example, corresponding to a Classical A1 to D4 Vita® shade guide.

The yttrium nitrate solution may have a yttrium nitrate concentration of 5 wt % to 90 wt %, more particularly 30 wt % to 85 wt %, and most particularly 50 wt % to 80 wt %. The yttrium chloride solution may have a yttrium chloride concentration of 5 wt % to 90 wt %, more particularly 30 wt % to 85 wt %, and most particularly 50 wt % to 80 wt %.

The polychromatic and polytranslucent ceramic blocks disclosed herein have a natural appearance and can be used for dental restorations, such as crowns, bridges, partial and full dentures.

Certain aspects are described below in the following numbered clauses:

1. A method comprising:
   - (a) obtaining a pre-shaded porous ceramic body comprising
     - i. a first end surface adjacent a first porous region, and
     - ii. a second end surface adjacent a second porous region, opposite the first end surface;
   - (b) infiltrating a yttrium nitrate aqueous solution through the first end surface to occupy the first porous region adjacent the first end;
   - (c) inverting the yttrium nitrate aqueous solution-infiltrated ceramic body;
   - (d) infiltrating water through the second end surface to occupy the second porous region adjacent the second end;
   - (e) contacting a portion of the yttrium nitrate aqueous solution in the first porous region with a portion of the infiltrating water in the second porous region at an interface; and
   - (f) forming within the interface a color/translucency gradient region resulting in a polychromatic/polytranslucent block.
2. The method of clause 1, wherein the pre-shaded porous ceramic body further comprises a side surface that is continuous between the first end and second end surfaces, and the method further comprises contacting and covering the second end surface and the side surface with a casing material, wherein the casing material contacting the second end surface and side surface prevents the yttrium nitrate aqueous solution from passing through the second end surface and the side surface; removing the casing material from the second end surface and side surface, inverting the ceramic body, and covering the first end surface and side surface with the casing material, wherein the casing material on the first end and the side surface prevents the water and the yttrium nitrate aqueous solution from passing through the first end surface and side surface.
3. The method of clause 1 or 2, wherein during infiltrating the yttrium nitrate aqueous solution, the first porous region is positioned above the second porous region, and the yttrium nitrate aqueous solution is infiltrated into the ceramic body through the first end surface downwardly into the first porous region.
4. The method of clause 3, further comprising inverting the porous ceramic body after infiltrating the yttrium nitrate aqueous solution into the first porous region above the second porous region, and the water is infiltrated from the second end surface downwardly into the second porous region.
5. The method of any one of clauses 1 to 4, comprising unidirectionally infiltrating the yttrium nitrate aqueous solution from the first end surface into the first porous region, and unidirectionally infiltrating the water from the second end surface into the second porous region, wherein the yttrium nitrate aqueous solution and the water are infiltrated sequentially.
6. The method of any one of clauses 1 to 5, comprising infiltrating between 3% by volume and 75% by volume porosity of the porous ceramic body with the yttrium nitrate aqueous solution, and infiltrating between 25% by volume and 97% by volume porosity of the porous ceramic body with the water.
7. The method of any one of clauses 1 to 6, wherein the porous ceramic body is a zirconia ceramic body.
8. The method of any one of clauses 1 to 7, wherein the yttrium nitrate aqueous solution has a yttrium nitrate concentration of 5 wt % to 90 wt %.
9. The method of any one of clauses 1 to 8, further comprising producing a dental restoration from the polychromatic/polytranslucent block wherein the first porous region corresponds to an incisal area of the dental restoration and the second porous region corresponds to a body area of the dental restoration.
10. The method of any of clauses 1 to 9, further comprising producing a dental restoration from the polychromatic/polytranslucent block wherein the interfacial color/translucency gradient region is between an incisal area and a cervical area of the dental restoration, and the interfacial color/translucency gradient region is the only the interfacial color/translucency gradient region present in the dental restoration.
11. The method of any one of clauses 1 to 10, wherein the pre-shaded porous ceramic body is a monochromatic porous ceramic body.
12. The method of any one of clauses 1 to 11, wherein the water infiltration time is longer than the yttrium nitrate aqueous solution infiltration time.
13. The method of any one of clauses 1 to 12, wherein the porous ceramic body is a bisque body.
14. The method of any one of clauses 1 to 13, further comprising repeating steps (a)-(f).
15. A method comprising:
   - (a) positioning a porous ceramic body within a casing, wherein the casing has a side wall and a bottom, and wherein the porous ceramic body comprises a side surface, a first end surface adjacent a first porous region, and a second end surface adjacent a second porous region opposite the first end surface, and the bottom and the side wall of the casing contact the second end surface and side surface of the porous ceramic body such that the side wall of the casing extends beyond the first end surface of the porous ceramic body and forms a reservoir;
   - (b) providing a volume of a yttrium nitrate aqueous solution within the reservoir on the first end surface of the porous ceramic body;

(c) infiltrating the yttrium nitrate aqueous solution through the first end surface of the ceramic body into a first porous region of the porous ceramic body, wherein the casing material prevents the yttrium nitrate aqueous solution from passing through the second end surface and the side surface of the porous ceramic body;

(d) inverting the porous ceramic body within the casing, wherein the first end surface is in contact with the bottom of the casing, and the side wall of the casing conforms to and contacts the side surface of the porous ceramic body;

(e) providing a volume of water within the reservoir on the second end surface;

(f) infiltrating the water through the second end surface into a second porous region that is adjacent the first porous region, wherein the casing material prevents the yttrium nitrate aqueous solution and the water from passing through the first end surface and the side surface of the porous ceramic body;

(g) contacting a portion of the water in the second porous region with a portion of the yttrium nitrate aqueous solution in the first porous region, and then mixing to form a color/translucency gradient region and (h) sintering the infiltrated porous ceramic body to form a sintered ceramic body comprising a first color/translucency region adjacent the first end surface, a second color/translucency region adjacent the second end surface, and a color/translucency gradient region there between.

16. The method of clause 15, comprising infiltrating between 3% by volume and 75% by volume porosity of the porous ceramic body with the yttrium nitrate aqueous solution, and infiltrating between 25% by volume and 97% by volume porosity of the porous ceramic body with the water.

17. The method of clause 15 or 16, wherein the porous ceramic body is a zirconia ceramic body.

18. The method of any one of clauses 15 to 17, wherein the yttrium nitrate aqueous solution has a yttrium nitrate concentration of 5 wt % to 90 wt %.

19. The method of any one of clauses 15 to 18, further comprising producing a dental restoration from the sintered ceramic body wherein the first porous region corresponds to an incisal area of the dental restoration and the second porous region corresponds to a body area of the dental restoration.

20. The method of any one of clauses 15 to 19, wherein the porous ceramic body is a monochromatic porous ceramic body.

21. The method of any one of clauses 15 to 19, wherein the porous ceramic body is pre-shaded.

22. The method of any one of clauses 15 to 20, further comprising repeating steps (a) to (g).

23. The method of any one of clauses 15 to 22, further comprising, between steps (g) and (h), subjecting the infiltrated porous ceramic body to a heat treatment cycle at a temperature that is below the sintering temperature and then milling the heat-treated ceramic body.

EXAMPLES

Example 1

Figure 3:
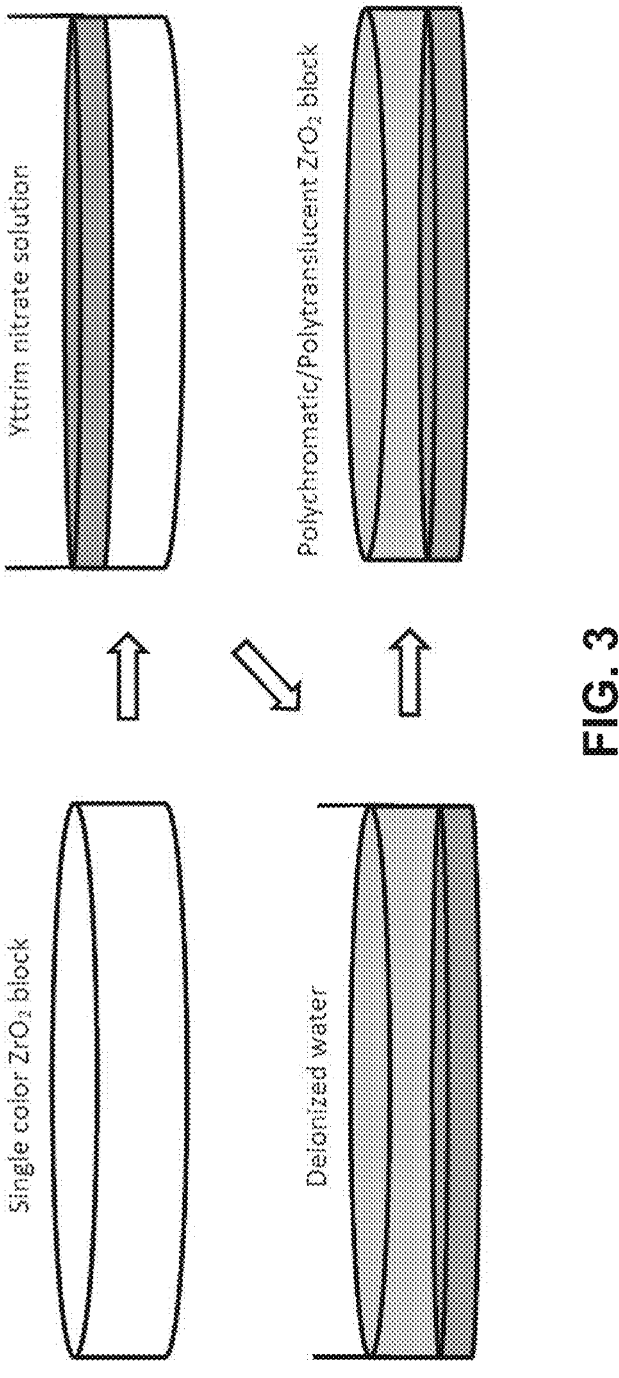
FIG. 3. Schematic diagram showing sequential, unidirectional infiltration of yttrium nitrate solution at one porous surface and then deionized water at the other porous surface of a pre-shaded $ZrO_2$ block to make a polychromatic/polytranslucent $ZrO_2$ block.

As can be seen in FIG. 3, a single colored $ZrO_2$ block was positioned inside of an infiltration setup. The infiltration setup is shown in FIGS. 2*a*, 2*b* and 2*c* and in U.S. Pat. No. 10,974,997, which patent is incorporated herein by reference. The pre-shaded $ZrO_2$ block (Bruxzir® Shaded 16+) is subjected to a sequential, unidirectional infiltration of yttrium nitrate solution and water. For example, a porous, bisqued, pre-shaded, $ZrO_2$ block is placed within a permeation-resistant casing material. In a first step, 75 wt % yttrium nitrate solution is placed over the surface of the first porous region and the yttrium nitrate solution is unidirectionally infiltrated in a downward direction into the surface of the first porous region. After the yttrium nitrate solution infiltration, the $ZrO_2$ body is inverted. In a second infiltration step, a volume of water is placed over the surface of the second porous region and then unidirectionally infiltrated downward toward the yttrium nitrate solution that infiltrated into the first porous region. Diffusion of the water into the yttrium nitrate solution contained within the first porous region forms a smooth transition region. The infiltrated yttrium nitrate solution at the incisal area increases the translucency of the incisal area with smooth translucency change at the transition zone resulting in polytranslucency. The infiltrated yttrium nitrate solution at the incisal area also weakens the color at incisal area with smooth color change at the transition zone resulting in a polychromatic effect in the block. The smooth polytranslucency and polychromacy at an interface area occur due to smooth diffusional mixing of water and yttrium nitrate solution at the interface area.

Figure 4A:
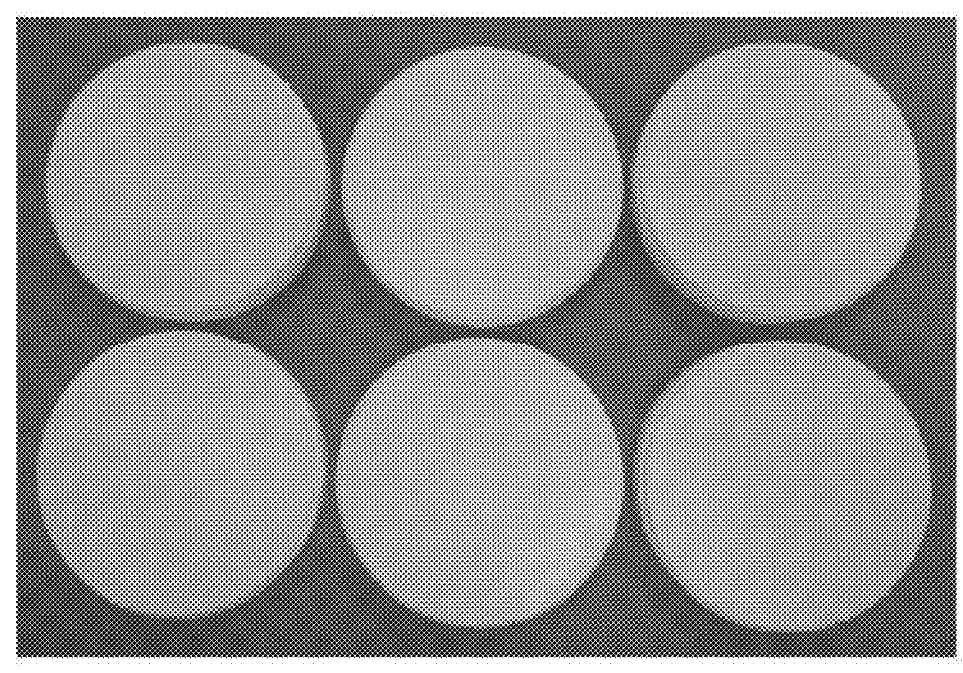
FIG. 4. (A) Top view and FIG. 4 (B) side view of 6 pieces of 98 mm blocks bisqued after sequential infiltration of yttrium nitrate solution at one porous surface and then water at the other porous surface to make polychromatic/polytranslucent $ZrO_2$ block.
Figure 4B:
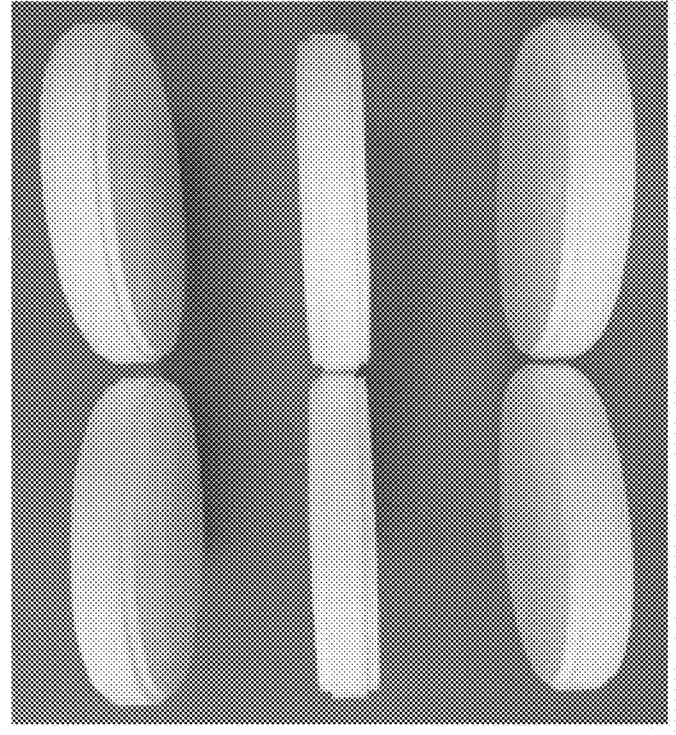

The infiltrated blocks were dried at 120° C. for 30 min, followed by heat treatment. The dried blocks were heated to 600° C. at a heating rate of 1° C./min, held for 1 hr at 600° C., and heated at 5° C./min to 850° C., and then cooled down from 850° C. without holding. As can be seen in FIGS. 4A and 4B, all the bisqued blocks showed smooth and clean surfaces without indicating any deformation such as bending, warpage, or delamination.

Example 2

To evaluate the effect of water infiltration on the formation of polychromatic/polytranslucent $ZrO_2$ block with smooth color/translucency gradient at interface, three pre-shaded $ZrO_2$ blocks with diameter of 98 mm and with thickness of 18 mm were infiltrated in different ways. The first block was an as-received, bisqued, pre-shaded, $ZrO_2$ block. The second block was a bisqued, pre-shaded block into which only one porous surface was infiltrated with yttrium nitrate solution without water infiltration. The third one was a block sequentially infiltrated with yttrium nitrate solution and water into the first porous region and second porous region, respectively. Three cubical samples with approximate size of 18 mm (thickness)×15 mm (width)×98 mm (length) were cut from the three bisqued 98 mm blocks. Three anterior crowns were also milled from the three bisqued 98 mm blocks. Three cubical block samples and three anterior crowns were sintered at 1580° C. for 2 hr 30 min. Optical micrographs of cross sections of sintered, three cubical blocks were taken, and the micrographs are shown in FIGS. 5A and 5B.

Figure 5A:
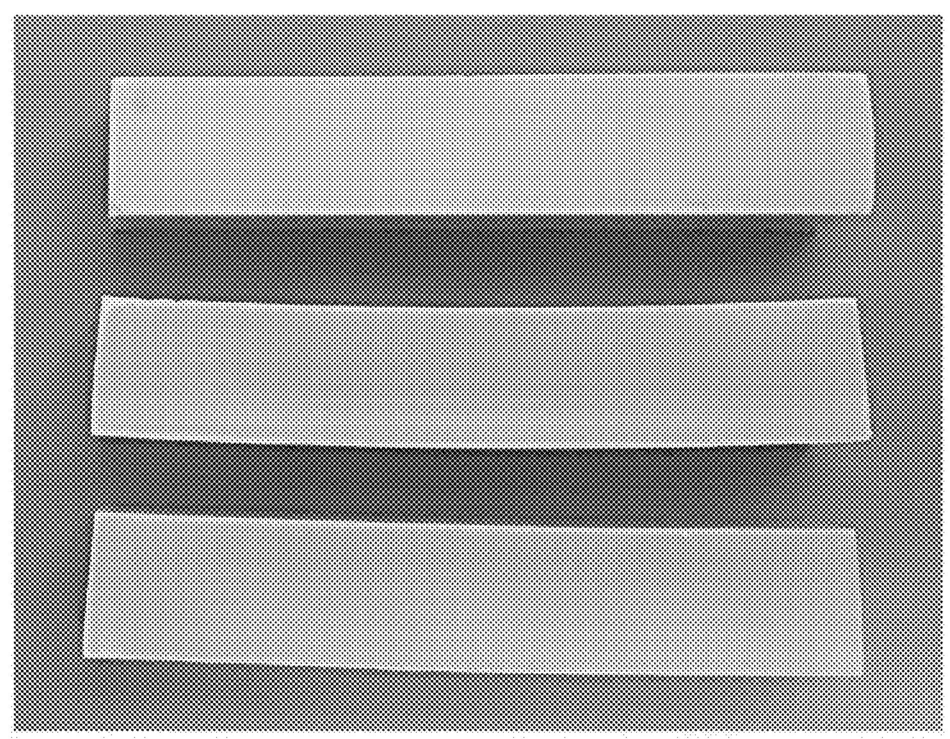
FIG. 5. (A) Optical micrograph of the cross sections of three cubical samples milled from 98 mm blocks with thickness of 18 mm after sintering at 1580° C. for 2 hr 30 min. top: cross section of sintered sample milled from pre-shaded block, middle: cross section of sintered sample milled from the pre-shaded block infiltrated only with yttrium nitrate solution at one porous surface, bottom: cross section of sintered sample milled from the pre-shaded block sequentially infiltrated with yttrium nitrate solution at one porous surface and then infiltrated with water at the other porous surface.
Figure 5B:
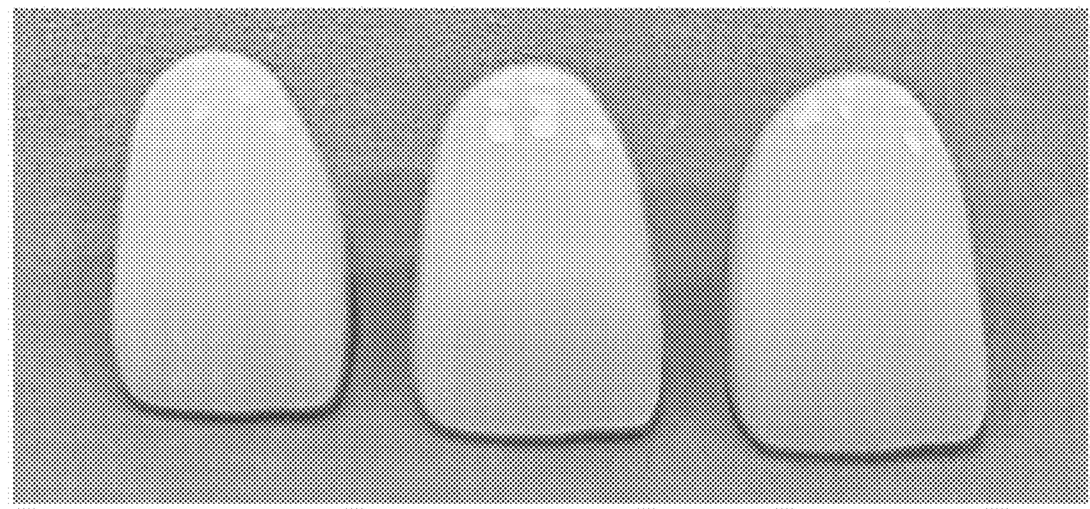

The cross section of sintered cubical sample milled from the pre-shaded 98 mm $ZrO_2$ block shows uniform A3 color all over the cross-sectional area (top of FIG. 5A). As can be seen in the middle of FIG. 5A, the sintered sample milled from a 98 mm $ZrO_2$ block infiltrated only with yttrium nitrate solution indicated a bending. It showed higher translucency and weakened color at incisal area due to infiltrated yttrium nitrate, but it indicated a sharp translucency and color change at interface area without smooth transition. As can be seen in the bottom of FIG. 5A, the cross section of the sintered cubical sample milled from a 98 mm $ZrO_2$ block sequentially infiltrated with yttrium nitrate solution and water indicated a minimized bending. The block showed higher translucency and weakened color at incisal area due to infiltrated yttrium nitrate solution with a smooth translucency and color change at interface area. All anterior crowns in FIG. 5B also showed correspondingly the same color and translucency changes as those observed in the block samples in FIG. 5A.

Example 3

Figure 6A:
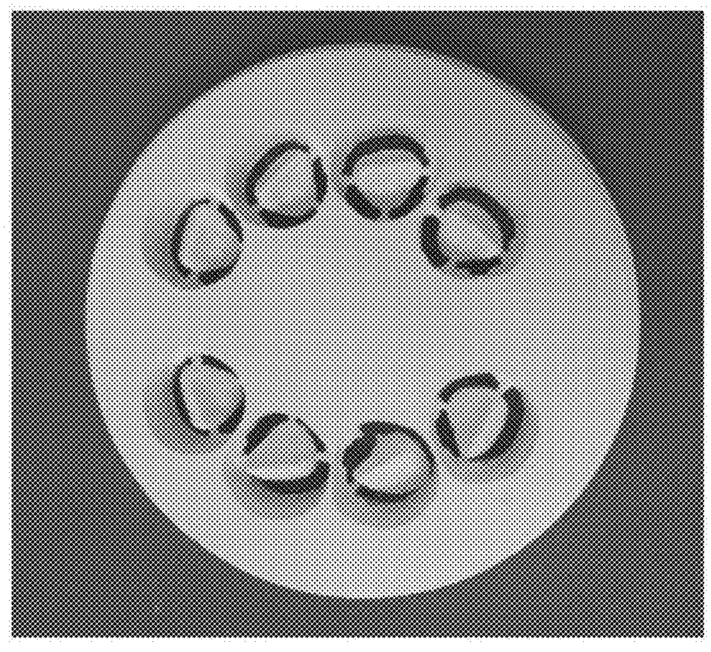
FIG. 6. (A) Optical micrograph of 8 anterior crowns milled from different locations at an infiltrated, polychromatic/polytranslucent, bisqued, 98 mm block, FIG. 6 (B) Optical micrograph of 10 anterior crowns sintered at 1580° C. for 2 hr 30 min. 8 anterior crowns at middle are the same polychromatic/polytranslucent crowns milled from different locations at an infiltrated block as shown in FIG. 6 (A). For comparison, two, sintered, pre-shaded crowns milled from a pre-shaded 98 mm block are also presented at most left and at most right position.
Figure 6B:
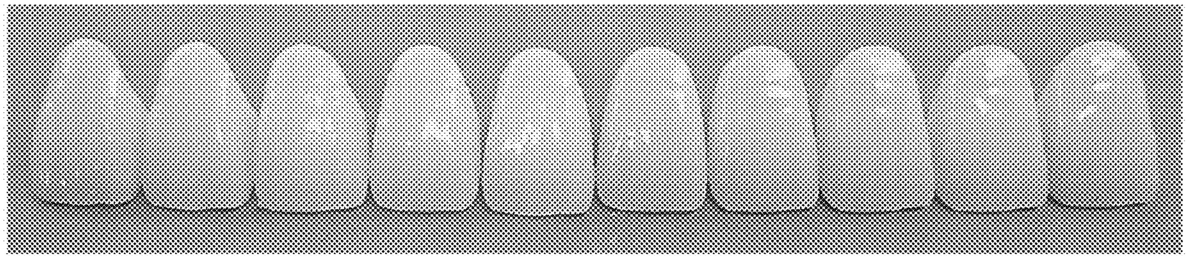

To evaluate homogeneity of the infiltration process in a block, eight anterior crowns were milled from different locations at the same infiltrated, bisqued, 98 mm block as shown in FIG. 6A. The eight milled crowns and two crowns milled from a pre-shaded block were sintered at 1580° C. for 2 hr 30 min and their optical micrograph is shown in FIG. 6B. The eight crowns showed similar color and translucency, indicating that the infiltration process in a block is homogeneous.

Example 4

Figure 7:
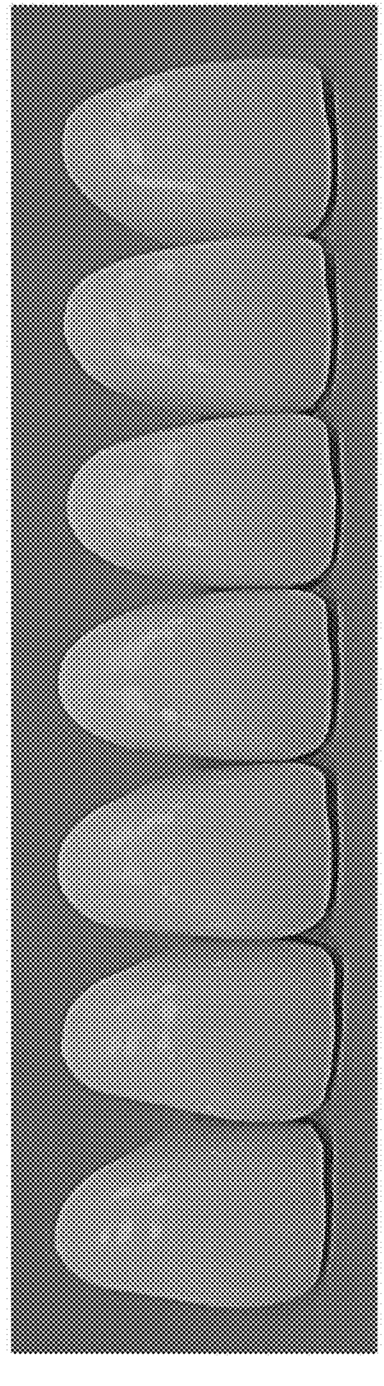
FIG. 7. Optical micrograph of sintered anterior crowns milled from blocks with incremental infiltration times of yttrium nitrate solution from left to right, 0 min, 5 min, 8 min, 10 min, 15 min, 30 min, and 60 min, respectively. As the time of infiltration increases, the height of incisal zone accordingly increases.

Seven pieces of porous, bisqued, pre-shaded $ZrO_2$ blocks were sequentially infiltrated with yttrium nitrate solution and water. All blocks were infiltrated with 75 wt % yttrium nitrate solution with different duration of 0 min, 5 min, 8 min, 10 min, 15 min, 30 min and 60 min, but the water was infiltrated with same duration for all seven blocks. As can be seen in FIG. 7, all crowns milled from blocks infiltrated with yttrium nitrate solution for different duration times showed smooth color and translucency change at interface. It also showed that as the time of infiltration increases, the height of incisal accordingly increases.

Example 5

The effect of infiltration of yttrium nitrate solution on the strength of $ZrO_2$ material was evaluated. For measuring strength of $ZrO_2$ at the body section of the crown, ten strength measurement bars were milled from an as-received, pre-shaded, porous, $ZrO_2$ block. For measuring strength of $ZrO_2$ at the incisal section of the crown, an as-received, pre-shaded, porous, $ZrO_2$ block was infiltrated with only 75 wt % yttrium nitrate solution into one porous surface for 2 hr, the block was dried at 120° C., and bisqued at 850° C., and then ten strength measurement bars were milled from the bisqued block. All twenty pieces of milled strength measurement bars were sintered at 1580° C. for 2 hr 30 min. The flexural strength measurement was conducted following ISO14704 standard. The average strength of body part of $ZrO_2$ was 1128±116 MPa, and the average strength of incisal part of the $ZrO_2$ was 543±53 MPa.

Figure 8:
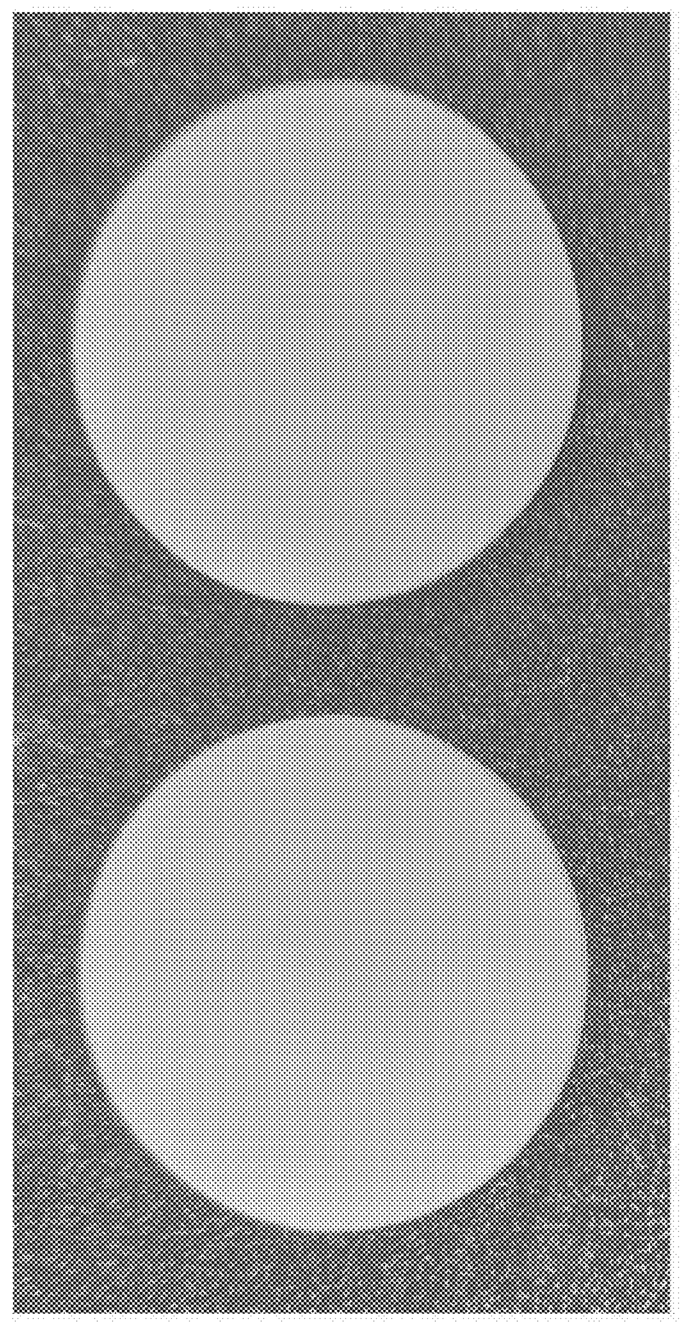
FIG. 8. Optical micrograph of two sintered discs for measuring translucencies of (left) body $ZrO_2$ and (right) incisal $ZrO_2$.

The effect of infiltration of yttrium nitrate solution on the translucencies of $ZrO_2$ material was also evaluated. For measuring translucency of $ZrO_2$ at the body section of the crown, a disc was milled from an as-received, pre-shaded, porous, $ZrO_2$ block. For measuring translucency of $ZrO_2$ at the incisal section of the crown, an as-received, pre-shaded, porous, $ZrO_2$ block was infiltrated with only 75 wt % yttrium nitrate solution into one porous surface for 2 hr, the block was dried at 120° C., and bisqued at 850° C., and a translucency disc was milled form the bisqued block. Two translucency discs were sintered at 1580° C. for 2 hr 30 min. The average translucency at 700 nm of body part of $ZrO_2$ was 44.9%, and the average translucency at 700 nm of incisal part of the $ZrO_2$ was 49.7%. The optical micrograph showing two discs for measuring translucencies of body and incisal part of $ZrO_2$ is shown in FIG. 8. As can be seen in FIG. 8 (right), the color of sample was weakened by infiltration of yttrium nitrate solution and the translucency increased.

Figure 9:
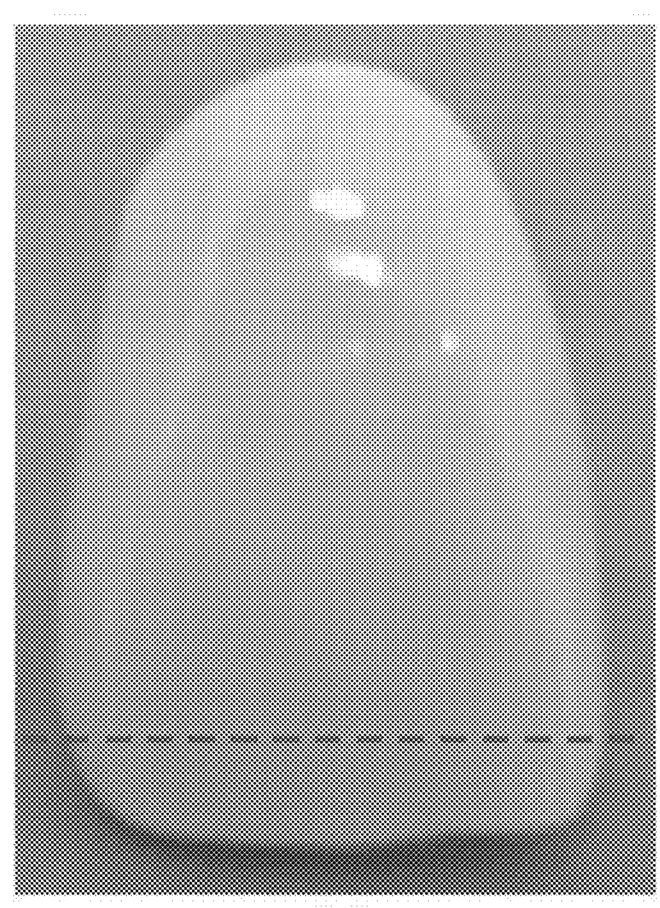
FIG. 9. Optical micrograph showing heights of body and incisal zone of polychromatic/polytranslucent anterior crown after infiltration of yttrium nitrate solution for 8 min.

As shown in FIG. 9, a blue line was drawn on the optical micrograph of anterior crown infiltrated with yttrium nitrate solution for 8 min indicates the top border line of incisal area. The blue line indicates that, after infiltration for 8 min, about 15% of the height of the anterior crown is incisal zone and about 85% of the height of the crown is body and transition zone. This means that about 85% of the polychromatic/polytranslucent crown has a higher strength of 1128±116 MPa and lower translucency of 44.9%, but only 15% of the crown has lower strength of 543±53 MPa and higher translucency of 49.7%.

Example 6

Figure 10:
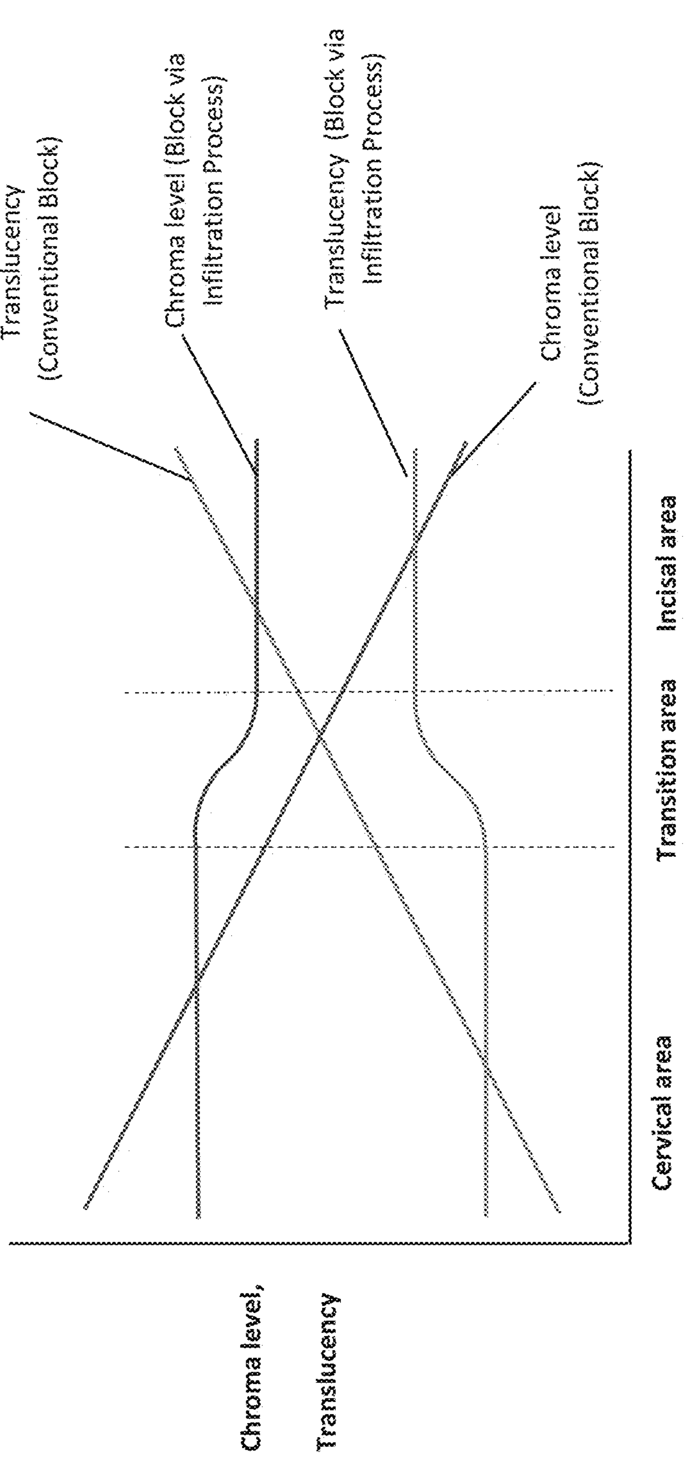
FIG. 10. Graphical comparison of chroma and translucency in a $ZrO_2$ block fabricated as disclosed herein (labeled "Block via Infiltration Process") and a comparative block made by a conventional polychromatic/polytranslucent block manufacturing process (labeled "Conventional Block").

Comparison of the translucency and chroma level in a block made by infiltration process disclosed herein and a comparative block made by a conventional process are compared and graphically summarized in FIG. 10.

This graph demonstrates that, for the block made by the infiltration processes disclosed herein, a color gradient and a translucency gradient is present only in the transition area; there are no color gradients or translucency gradients in the cervical area or the incisal area. In contrast, the block manufactured using conventional processes has a color gradient and a translucency gradient throughout the full thickness of the block.

Example 7

As can be seen in FIG. 3, a bisqued, porous, single colored $ZrO_2$ block was positioned inside of an infiltration setup. The infiltration setup is shown in FIGS. 2A, 2B and 2C. The pre-shaded $ZrO_2$ block (Brux Shaded 16+) is subjected to a sequential, unidirectional infiltration of yttrium chloride solution and water. For example, a porous, bisqued, pre-shaded, $ZrO_2$ block is placed within a permeation-resistant casing material. In a first step, 65 wt % yttrium chloride solution is placed over the surface of the first porous region and the yttrium chloride solution is unidirectionally infiltrated in a downward direction into the surface of the first porous region. After the yttrium chloride solution infiltration, the $ZrO_2$ body is inverted. In a second infiltration step, a volume of water is placed over the surface of the second porous region and then unidirectionally infiltrated downward toward the yttrium chloride solution that infiltrated into the first porous region. Diffusion of the water into the yttrium chloride solution contained within the first porous region forms a smooth transition region. The infiltrated yttrium chloride solution at the incisal area increases the translucency of the incisal area with smooth translucency change at the transition zone resulting in polytranslucency. The infiltrated yttrium chloride solution at the incisal area also weakens the color at incisal area with smooth color change at the transition zone resulting in a polychromatic effect in the block. The smooth polytranslucency and polychromacy at an interface area occur due to smooth diffusional mixing of water and yttrium chloride solution at the interface area.

The infiltrated blocks were dried at 120° C. for 120 min without any further bisquing heat treatment. All the dried blocks showed smooth and clean surfaces without indicating any deformation such as bending, warpage, or delamination. After drying at 120° C. for 120 min, the blocks successfully could be milled without tool breakage.

Example 8

As an alternative way of achieving a smooth transition at interface, a different infiltration procedure was conducted. As can be seen in FIG. 3, a bisqued, porous, single colored $ZrO_2$ block was positioned inside of an infiltration setup. The infiltration setup is shown in FIGS. 2A, 2B and 2C. A porous, bisqued, pre-shaded, $ZrO_2$ block is placed within a permeation-resistant casing material. In a first step, water is placed over the surface of the first porous region and the water is unidirectionally infiltrated for short period of time, e.g., 20 sec, in a downward direction into the surface of the first porous region. After the water infiltration for a short period of time, the excess water is decanted, and the $ZrO_2$ block is not inverted. In a second infiltration step, a volume of 65 wt % yttrium chloride solution is placed over the surface of the first porous region and then unidirectionally infiltrated downward direction for a longer period of time, e.g., min. After yttrium chloride infiltration, the block was removed from the casing, inverted, and repositioned within the casing the inverted position letting water diffuse into the yttrium chloride solution. However, the diffusion of yttrium chloride solution into the lower viscosity water during the relatively longer time, 10 minutes, of yttrium chloride solution infiltration, resulted in an undesirable, wider, diffuse interface region.

Example 9

As a way of achieving a smooth transition at interface which has a desirable, controlled, optimum width, a different infiltration procedure was conducted. As can be seen in FIG. 3, a bisqued, porous, single colored $ZrO_2$ block was positioned inside of an infiltration setup. The infiltration setup is shown in FIGS. 2A, 2B and 2C. A porous, bisqued, pre-shaded, $ZrO_2$ block is placed within a permeation-resistant casing material. In a first step, a water-ethylene glycol mixture (e.g. 30 wt % ethylene glycol/70 wt % water) which has a higher viscosity than water alone is placed over the surface of the first porous region and the water-ethylene glycol mixture is unidirectionally infiltrated for relatively short period of time, e.g., 2 min, in a downward direction into the surface of the first porous region. After the water-ethylene glycol mixture infiltration for a relatively short period of time, the excess mixture is decanted and the $ZrO_2$ body is not inverted. In a second infiltration step, without inverting the block, a volume of 65 wt % yttrium chloride solution is placed over the surface of the first porous region and then unidirectionally infiltrated downward direction for a longer period of time, e.g., 10 min. After the yttrium chloride infiltration, the block was removed from the casing, inverted, and then repositioned within the casing in the inverted position, letting the water-ethylene glycol mixture diffuse into the yttrium chloride solution. Because of the increased viscosity of the water-ethylene glycol mixture, the diffusion of yttrium chloride solution into the water-ethylene glycol mixture was slowed down in a controllable way resulting in a smooth, controlled, and spatially-restricted interface region.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for making a polychromatic/polytranslucent ceramic block from a pre-shaded porous ceramic body, comprising:

(a) obtaining a pre-shaded porous ceramic body comprising
 i. a first end surface adjacent a first porous region, and
 ii. a second end surface adjacent a second porous region, opposite the first end surface; and (b)(1) infiltrating a yttrium-containing solution through the first end surface to occupy the first porous region adjacent the first end thereby weakening a chroma level and increasing a translucency of the first porous region;

(c)(1) after infiltrating the yttrium-containing solution through the first end surface, inverting the yttrium-containing solution-infiltrated ceramic body;

(d)(1) after inverting the yttrium-containing solution-infiltrated ceramic body, infiltrating water through the second end surface to occupy the second porous region adjacent the second end thereby not changing a chroma level or a translucency of the second porous region;

(e)(1) contacting a portion of the yttrium-containing solution in the first porous region with a portion of the infiltrating water in the second porous region at an interface; and (f)(1) forming within the interface a chroma/translucency gradient region resulting in a polychromatic/polytranslucent ceramic block.

2. The method of claim 1, wherein the pre-shaded porous ceramic body further comprises a side surface that is continuous between the first end and second end surfaces, and the method further comprises contacting and covering the second end surface and the side surface with a casing material, wherein the casing material contacting the second end surface and side surface prevents the yttrium-containing solution from passing through the second end surface and the side surface; removing the casing material from the second end surface and side surface, inverting the ceramic body, and covering the first end surface and side surface with the casing material, wherein the casing material on the first end and the side surface prevents the water and the yttrium-containing solution from passing through the first end surface and side surface.

3. The method of claim 1, comprising infiltrating between 3% by volume and 75% by volume porosity of the porous ceramic body with the yttrium-containing solution, and infiltrating between 25% by volume and 97% by volume porosity of the porous ceramic body with the water.

4. The method of claim 1, wherein the porous ceramic body is a zirconia ceramic body.

5. The method of claim 1, wherein the yttrium-containing solution comprises yttrium nitrate.

6. The method of claim 1, wherein the yttrium-containing solution comprises yttrium chloride.

7. The method of claim 1, further comprising producing a dental restoration from the polychromatic/polytranslucent block wherein the first porous region corresponds to an incisal area of the dental restoration and the second porous region corresponds to a body area of the dental restoration.

8. The method of claim 1, further comprising producing a dental restoration from the polychromatic/polytranslucent block wherein the interfacial color/translucency gradient region is between an incisal area and a cervical area of the dental restoration, and the interfacial color/translucency gradient region is the only the interfacial color/translucency gradient region present in the dental restoration.

9. The method of claim 1, wherein the pre-shaded porous ceramic body is a monochromatic porous ceramic body.

10. A method for making a polychromatic/polytranslucent ceramic block from a pre-shaded porous ceramic body comprising:

(a) positioning a pre-shaded porous ceramic body within a casing, wherein the casing has a side wall and a bottom, and wherein the pre-shaded porous ceramic body comprises a side surface, a first end surface adjacent a first porous region, and a second end surface adjacent a second porous region opposite the first end surface, and the bottom and the side wall of the casing contact the second end surface and side surface of the pre-shaded porous ceramic body such that the side wall of the casing extends beyond the first end surface of the pre-shaded porous ceramic body and forms a reservoir;

(b) providing a volume of a yttrium-containing solution within the reservoir on the first end surface of the pre-shaded porous ceramic body;

(c) infiltrating the yttrium-containing solution through the first end surface of the pre-shaded porous ceramic body into a first porous region of the pre-shaded porous ceramic body thereby weakening a chroma level and increasing a translucency of the first porous region, wherein the casing material prevents the yttrium-containing solution from passing through the second end surface and the side surface of the pre-shaded porous ceramic body;

(d) after infiltrating the yttrium-containing solution through the first end surface of the pre-shaded porous ceramic body, inverting the pre-shaded porous ceramic body within the casing, wherein the first end surface is in contact with the bottom of the casing, and the side wall of the casing conforms to and contacts the side surface of the pre-shaded porous ceramic body;

(e) after inverting the pre-shaded porous ceramic body, providing a volume of water within the reservoir on the second end surface;

(f) infiltrating the water through the second end surface into a second porous region that is adjacent the first porous region thereby not changing a chroma level or a translucency of the second porous region, wherein the casing material prevents the yttrium-containing solution and the water from passing through the first end surface and the side surface of the pre-shaded porous ceramic body;

(g) contacting a portion of the water in the second porous region with a portion of the yttrium-containing solution in the first porous region at an interface between the first porous region and the second porous region, and then mixing to form a color/translucency gradient region and (h) sintering the infiltrated pre-shaded porous ceramic body to form a sintered ceramic body comprising a first color/translucency region adjacent the first end surface, a second color/translucency region adjacent the second end surface, and a color/translucency gradient region there between.

* * * * *